(12) United States Patent
Mountney et al.

(10) Patent No.: US 10,262,453 B2
(45) Date of Patent: Apr. 16, 2019

(54) VIRTUAL SHADOWS FOR ENHANCED DEPTH PERCEPTION

(71) Applicants: Peter Mountney, London (GB); Thomas Engel, Aalen (DE); Philip Mewes, Nürnberg (DE); Thomas Pheiffer, Langhorne, PA (US)

(72) Inventors: Peter Mountney, London (GB); Thomas Engel, Aalen (DE); Philip Mewes, Nürnberg (DE); Thomas Pheiffer, Langhorne, PA (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/468,810

(22) Filed: Mar. 24, 2017

(65) Prior Publication Data
US 2018/0276877 A1  Sep. 27, 2018

(51) Int. Cl.
G06T 15/60 (2006.01)
G06T 17/10 (2006.01)
(Continued)

(52) U.S. Cl.
CPC .......... *G06T 15/60* (2013.01); *A61B 1/00009* (2013.01); *A61B 34/20* (2016.02); *G06T 7/70* (2017.01); *G06T 15/506* (2013.01); *G06T 17/10* (2013.01); *G06T 19/00* (2013.01); *G06T 19/006* (2013.01); *H04N 13/275* (2018.05); *A61B 1/00045* (2013.01); *G06T 2207/10028* (2013.01); *G06T 2207/10068* (2013.01);
(Continued)

(58) Field of Classification Search
None
See application file for complete search history.

(56) References Cited

U.S. PATENT DOCUMENTS 9,646,423 B1 * 5/2017 Sun ....................... G06T 19/006
2002/0139920 A1 10/2002 Seibel et al.
(Continued)

FOREIGN PATENT DOCUMENTS

WO  WO2017157970 A1  9/2017

OTHER PUBLICATIONS

Www.helloweb.co.kr, Design by HelloWeb—. "Laser / LED Hybrid Technology—ML-L ARISTO-L3." MGB Endoskopische Geräte GmbH Berlin. N.p., Oct. 13, 2016. Web. Apr. 6, 2017.
(Continued)

*Primary Examiner* — Kee M Tung
*Assistant Examiner* — Yanna Wu
(74) *Attorney, Agent, or Firm* — Lempia Summerfield Katz LLC (57) ABSTRACT

In order to improve depth perception for an image displayed during a laparoscopic surgery, a representation of a shadow of a tool included in the image and used in the laparoscopic surgery is identified and introduced into the image. A processor augments a three-dimensional (3D) model including a 3D representation of a surface of an object included in the image, and a representation of the tool by introducing a virtual light source into the 3D model to generate a virtual shadow within the 3D model. The processor subtracts the representation of the shadow out of the augmented 3D model and superimposes the representation of the shadow on the image to be displayed during the laparoscopic surgery.

20 Claims, 6 Drawing Sheets

(51) Int. Cl.
G06T 7/70 (2017.01)
H04N 13/275 (2018.01)
G06T 15/50 (2011.01)
G06T 19/00 (2011.01)
A61B 1/00 (2006.01)
A61B 34/20 (2016.01)

(52) U.S. Cl.
CPC ........... G06T 2207/30204 (2013.01); G06T 2210/41 (2013.01); G06T 2215/12 (2013.01); G06T 2215/16 (2013.01)

(56) References Cited

U.S. PATENT DOCUMENTS

| | | | |
|---|---|---|---|
| 2010/0315413 A1* | 12/2010 | Izadi | G06F 3/017 345/419 |
| 2013/0123801 A1 | 5/2013 | Umasuthan et al. | |
| 2015/0015581 A1* | 1/2015 | Lininger | G06T 11/00 345/426 |
| 2016/0191887 A1 | 6/2016 | Casas | |
| 2017/0046833 A1* | 2/2017 | Lurie | G06T 19/20 |
| 2018/0020992 A1* | 1/2018 | Guo | A61B 5/7425 |

OTHER PUBLICATIONS

Bimber, Oliver et al. "Consistent Illumination within Optical See-Through Augmented Environment" Proceedings of the Second IEEE and ACM International Symposium on Mixed and Augmented Reality: 2003, Tokyo, Japan, IEEE Computer Society, Los Alamitos, Calif. [U.A.], XP058187377; ISBN: 978-0-7695-2006-3; 2003.

DeBevec, Paul "Rendering Synthetic Objects into Real Scenes: Bridging Traditional and Image-based Graphics with Global Illumination and High Dynamic Range Photography"; SIGGRAPH 98 conference proceedings, pp. 1-10, KP058345126, ; University of California at Berkeley.

Hanna, George B., et al. "Shadow depth cues and endoscopic task performance." Archives of Surgery 137.10 (2002): 1166-1169.

Mishra, Rajineesh K. et al. "Optimum Shadow-Casting Illumination for Endoscopic Task Performance" Arch Surg., vol. 139, No. 8, pp. 889-892, 2004; doi:10.1001/archsurg.139.8.889.

Navab, Nassir et al. "Laparoscopic Virtual Mirror New Interaction Paradigm for Monitor Based Augmented Reality" IEEE Virtual Reality Conference 2007, pp. 43-50; DOI 10.1109/VR.2007. 352462; 2007.

Nicolaou, Marios et al. "Invisible Shadow for Navigation and Planning in Minimal Invasive Surgery" J. Duncan and G. Gerig (Eds.); MICCAI 2005; LNCS 3750, pp. 25-32; Springer-Verlag Berlin Heidelberg 2005.

PCT International Search Report and Written Opinion of the International Searching Authority dated May 22, 2018, for corresponding PCT/EP2018/053856.

* cited by examiner

VIRTUAL SHADOWS FOR ENHANCED DEPTH PERCEPTION

FIELD

The present embodiments relate to a method for generating virtual shadows on an image.

BACKGROUND

Laparoscopic and endoscopic cameras are used to see inside the body of a patient for surgery and diagnostics. Laparoscopic and endoscopic cameras generate essentially two-dimensional (2D) images of three-dimensional (3D) anatomy. During a surgery, an operator (e.g., a surgeon) guides tools to target regions inside the body of the patient to, for example, cut tissue, make dissections, and/or take biopsies based on a 2D image stream generated with the laparoscopic camera and/or the endoscopic camera. With the 2D image stream, the sense of depth and 3D is lost. This makes navigating and controlling the tools difficult for the operator.

Current approaches to improving depth perception include creating 3D visualizations and introducing missing depth cues such as a motion parallax or a shadow. 3D visualizations are created with a stereo laparoscopic camera, and 3D displays are used. The 3D displays may make the operator nauseous, and have limited working volumes, making the 3D displays challenging to integrate into an operating room or work with multiple team members. Also, some 3D displays require the operator to wear glasses, which may cause discomfort during long procedures.

Motion parallax and motion perspective may be reintroduced with a virtual mirror. The use of the virtual mirror, however, requires registration of a pre-operative model to the patient, and the virtual mirror is configured to be used with augmented reality. Shadows may be reintroduced with additional lights on the laparoscopic camera. Because the additional lights are co-aligned with the laparoscopic camera, the strength of the shadows that are cast is limited and the direction of the shadows may not be optimal.

SUMMARY

In order to improve depth perception for an image displayed during a laparoscopic surgery, a representation of a shadow of a tool included in the image and used in the laparoscopic surgery is artificially created and introduced into the image. A processor generates a three-dimensional (3D) model including a 3D representation of a surface of an object included within the image with a structured light endoscope. The processor determines a position of the tool and introduces a representation of the tool into the 3D model based on the determined position. The processor augments the 3D model by introducing a virtual light source into the 3D environment to generate a shadow projected onto the 3D model. The processor identifies the representation of the shadow from the augmented 3D model and adds the representation of the shadow to the image to be displayed during the laparoscopic surgery.

In a first aspect, a method for augmenting an image of a surface of an object is provided. The method includes identifying, by a processor, the image of the surface of the object. The image of the surface of the object is an image of the surface of the object and at least a portion of a tool. The processor identifies a three-dimensional (3D) model of the surface of the object. The processor generates a first augmented 3D model. The generating of the first augmented 3D model includes superimposing a representation of the tool on the identified 3D model of the surface of the object. The processor introduces a virtual light source into the generated first augmented 3D model. The processor generates a second augmented 3D model. The generating of the second augmented 3D model includes generating a representation of a shadow on the surface of the object in the generated first augmented 3D model based on the virtual light source introduced into the generated first augmented 3D model. The processor augments the identified image of the surface of the object. The augmenting of the identified image of the surface of the object includes superimposing the generated representation of the shadow on the identified image of the surface of the object and the tool.

In a second aspect, a non-transitory computer-readable storage medium stores instructions executable by one or more processors to augment an image of a surface of an object. The instructions include identifying, by a processor, the image of the surface of the object. The image of the surface of the object is an image of the surface of the object and at least a portion of a tool. The tool is adjacent to the surface of the object. The instructions further include identifying, by the processor, a 3D model of the surface of the object, and superimposing, by the processor, a representation of the tool on the identified 3D model of the surface of the object. The instructions include introducing, by the processor, a virtual light source into the superimposed representation of the tool and identified 3D model of the surface of the object. The instructions further include generating, by the processor, a representation of a shadow on the surface of the object within the superimposed representation of the tool and identified 3D model of the surface of the object based on the introduced light source. The instructions include superimposing, by the processor, the generated representation of the shadow on the identified image of the surface of the object and the tool.

In a third aspect, a system for generating an augmented image of a surface of an object and at least a portion of a tool is provided. The system includes a memory configured to store an image of the surface of the object and at least the portion of the tool, and a 3D model of the surface of the object. The system also includes a processor in communication with the memory. The processor is configured to superimpose a representation of the tool on the identified 3D model of the surface of the object. The processor is also configured to introduce a virtual light source into the superimposed representation of the tool and the identified 3D model of the surface of the object. The processor is configured to generate a representation of a shadow on the surface of the object within the superimposed representation of the tool and identified 3D model of the surface of the object based on the introduced light source, and is configured to superimpose the generated representation of the shadow on the stored image of the surface of the object and at least the portion of the tool.

DETAILED DESCRIPTION OF THE DRAWINGS

The present embodiments may be used to introduce a depth cue into a laparoscopic video and thus create an enhanced visualization during, for example, a laparoscopic surgery. The depth cue may be, for example, a virtual shadow. To generate the virtual shadow, a processor identifies a three-dimensional (3D) model of a tissue surface within a body to be imaged and a position of a tool to be used during the laparoscopic surgery in a same coordinate system.

The 3D model of the tissue surface is generated with, for example, a structured light endoscope. The structured light endoscope generates a point cloud of the tissue surface the structured light endoscope is observing. A processor generates a mesh for the 3D model of the tissue surface. Alternatively, a stereo endoscope or a monocular scope using temporal information may generate the 3D model of the tissue surface.

The position of the tool may be estimated using a tracking system. The tracking system may include, for example, an optical tracker including one or more cameras and tracker markers placed on a proximal end of the tool. From positions of the markers and a 3D model of the tool, the position of the tool in 3D space may be estimated. Through a calibration process, a position of a tip of the tool in the 3D space may be estimated. In order to generate the virtual shadow, the position of the tool relative to the 3D model of the tissue surface is to be known. Accordingly, the structured light endoscope may also include one or more tracker markers.

A number of models of different tools may be generated off-line and saved in a memory. The processor may identify one of the stored models that corresponds to the tool being used. Alternatively, the processor may determine a shape and a size of the tool based on one or more images generated by a laparoscope (e.g., the structured light endoscope), and the processor may generate a model of the tool during the laparoscopic surgery, for example.

The model of the tool is introduced into the 3D model of the surface of the tissue based on the determined position of the tool in the 3D space. A virtual light source is introduced into the 3D model of the surface of the tissue. The virtual light source may be positioned in any number of positions within the 3D model of the surface of the tissue including, for example, in an up vector from a corresponding laparoscopic camera image or at a position upward of gravity as defined by the optical tracker.

The light from the virtual light source causes a virtual shadow to be cast onto the representation of the tissue within the 3D model of the surface of the tissue. The 3D model of the surface of the tissue may be rendered from a viewpoint of the laparoscope to be used during the laparoscopic surgery (e.g., the structured light laparoscope). The 3D model of the surface of the tissue is rendered with and without the shadow, and the 3D model without the shadow is subtracted from the 3D model with the shadow. This subtraction of the models generates the virtual shadow. The virtual shadow is then blended or fused with an image generated with, for example, the structured light laparoscope to generate a virtual shadow augmented image.

The introduction of virtual shadows into images generated by a laparoscope enables surgical procedures to be performed faster and more efficiently with fewer errors compared to prior art techniques for improving depth perception when viewing laparoscopic images and/or videos. The introduction of virtual shadows also makes learning laparoscopic surgical techniques and skills easier.

Figure 1:
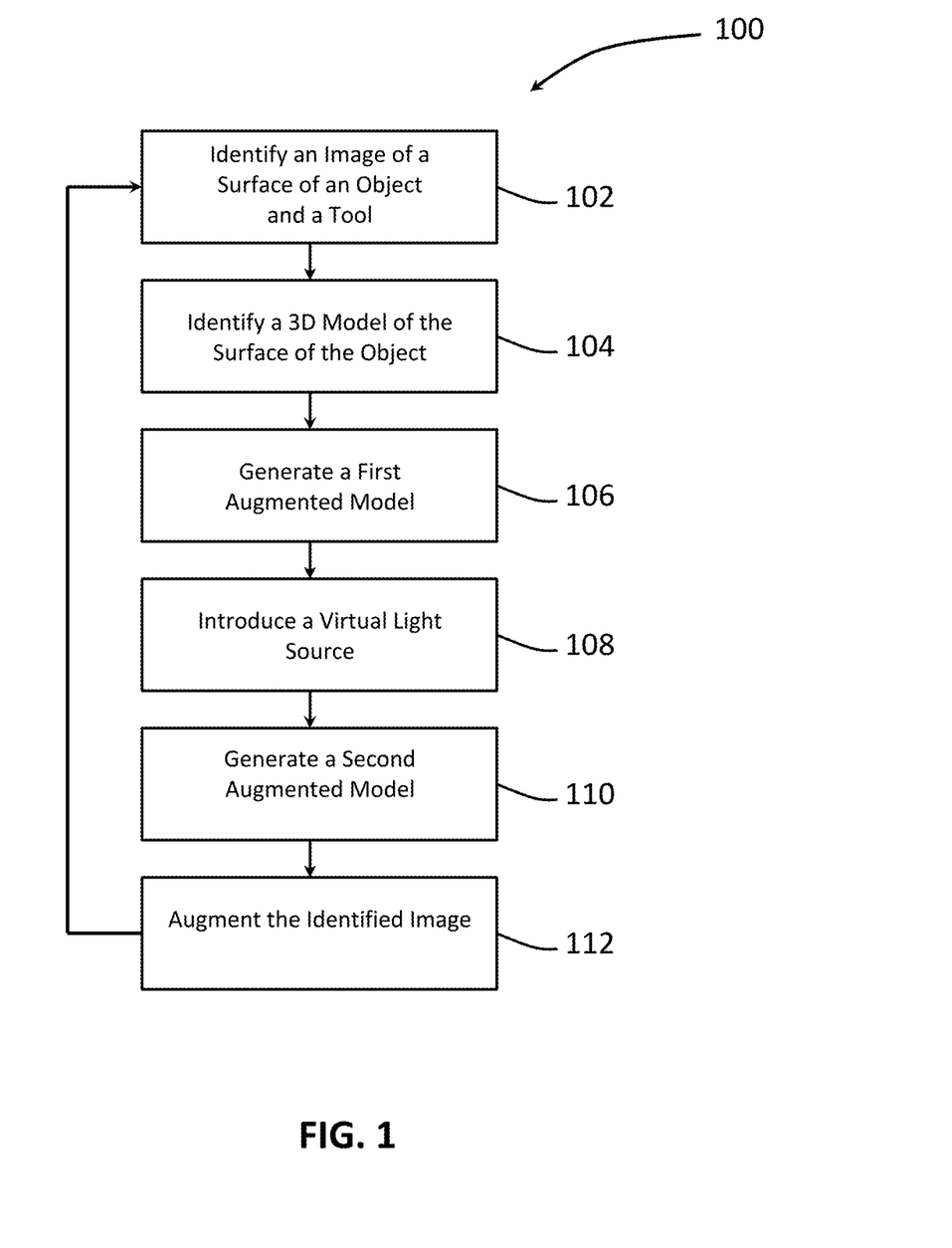
FIG. 1 shows a flowchart of one embodiment of a method for augmenting an image of a surface of an object with a virtual image.

FIG. 1 shows a flowchart of one embodiment of a method 100 for augmenting an image of a surface of an object with a virtual image. The method 100 may be performed using an imaging system shown in FIGS. 8 and 9 or another imaging system. The method is implemented in the order shown, but other orders may be used. Additional, different, or fewer acts may be provided. Similar methods may be used for augmenting an image with a virtual shadow.

In act 102, a processor identifies an image of the surface of the object and a tool being used during a medical procedure. Within the image, the tool is adjacent to the surface of the object. For example, the medical procedure may be a laparoscopic surgery. Laparoscopic surgery is a minimally invasive surgery that includes operations within abdominal or pelvic cavities. During the laparoscopic surgery, a laparoscope and/or a tool are inserted into the object (e.g., a body of a patient). The tool may be any number of medical devices including, for example, a trocar, forceps, scissors, a probe, a dissector, hooks, retractors, or other medical devices.

In one embodiment, identifying the image of the surface of the object includes a first endoscope generating 2D image data representing the surface of the object. The first endoscope may be any number of different types of endoscopes including, for example, a structured light endoscope, a monocular laparoscope, a stereo scope, or another imaging device. The first endoscope may be inserted into the patient, for example, via a small incision and a port installed at the incision. A light source as part of the first endoscope or a separate light source may also be introduced into the patient to illuminate the tissue to be imaged. In another embodiment, a plurality of images of the surface of the object are stored in a memory in communication with the processor, and the processor identifies the image of the surface of the object from the plurality of images of the surface stored in the memory.

Figure 2:
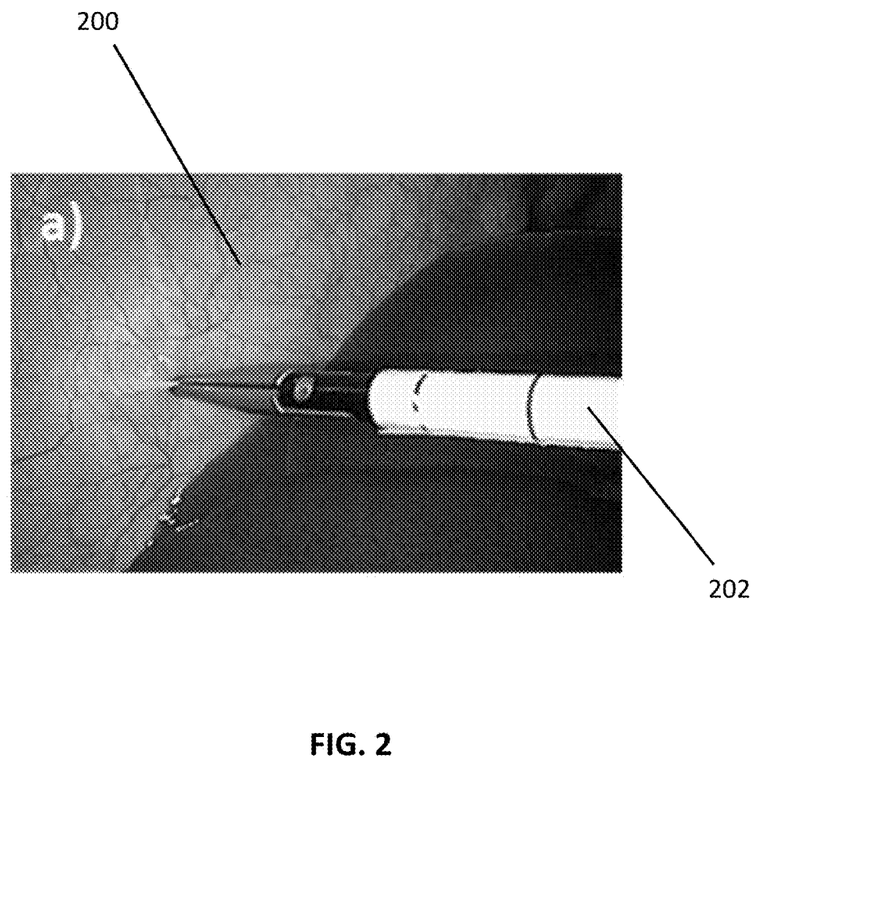
FIG. 2 is an example of an image of a surface of an object and a tool being used during a medical procedure.

FIG. 2 is an example of an image of a surface of an object 200 and a tool 202 being used during a medical procedure. The object 200 may, for example, be any number of organs within a human body. For example, the object 200 may be the uterus, spleen, gallbladder, or another organ within the abdomen of the patient. As shown in FIG. 2, the image generated by the first endoscope, for example, is essentially a 2D image of a 3D anatomy. With 2D images, the sense of depth and 3D is lost, which makes navigating difficult for a user (e.g., a surgeon). As shown in FIG. 2, the image generated by the first endoscope includes a faint shadow or no shadow at all.

In act 104, the processor identifies a 3D model of the surface of the object. In one embodiment, identifying the 3D model of the surface of the object includes a second endoscope generating data representing the surface of the object. The second endoscope may be any number of types of endoscopes including, for example, a structured light laparoscope. Other types of endoscopes such as, for example, a stereo scope or a monocular laparoscope may be used to generate the data representing the surface of the object. In one embodiment, the second endoscope and the first endoscope are the same endoscope. For example, the structured light endoscope may include a camera that operates at 60 frames/s. The image from act 102 is generated every other frame, and the data for the 3D model from act 102 is generated the other frames.

In one embodiment, the structured light laparoscope, for example, generates a point cloud of the surface of the object. The point cloud represents 3D coordinates of points on an external surface of the object. The structured light laparoscope measures a large number of points on the external surface of the object and outputs the point cloud as a data file.

The processor generates a mesh of the surface of the object based on the point cloud generated by the structured light laparoscope. The processor generates the 3D model of the surface of the object based on the generated mesh. In one embodiment, the processor generates the 3D model of the surface from a viewpoint from which the image of the surface of the object and a tool identified in act 102 is imaged. In other words, the 3D model of the surface is generated such that the 3D model of the surface and the image identified in act 102 are from the same viewpoint.

In act 106, the processor generates a first augmented 3D model. The generating of the first augmented 3D model includes superimposing a representation of the tool on the identified 3D model of the surface of the object. The processor identifies a position of the tool and the representation of the tool.

In one embodiment, an optical tracking system identifies a 3D position of the tool relative to the 3D model of the surface of the object. The optical tracking system includes one or more cameras positioned at a distance away from the object being imaged. In one embodiment, the optical tracking system includes two or more cameras that provide overlapping projections. The processor uses image data generated by the two cameras to triangulate, for example, the 3D position of the tool relative to the 3D model of the surface of the object.

The optical tracking system may include one or more (e.g., four) markers positioned on the tool. In one embodiment, the optical tracking system may also include one or more (e.g., four) markers positioned on, for example, the structured light endoscope. The four markers, for example, may be optical markers that are visible within images generated by the cameras. The one or more markers positioned on the tool and/or the one or more markers positioned on the structured light endoscope may be any number of sizes and shapes. For example, the one or more markers positioned on the tool and the one or more markers positioned on the structured light endoscope are spherical and are large enough to be visible within images generated by the two or more cameras. In other embodiments, the 3D position of the tool is identified in other ways. For example, a tracking system identifies a 3D position of the tool relative to the 3D model of the surface of the object with electromagnetic (EM) trackers, mechanical trackers, shape sensors, or other types of trackers instead of or in addition to the optical tracking system.

The processor triangulates the 3D position (e.g., 3D coordinates within a 3D space) of the tool and/or the 3D position (e.g., 3D coordinates within a 3D space) of the structured light endoscope based on image data generated by the two cameras, which includes representations of the markers on the tool and/or the markers on the structured light endoscope, and representations of markers with known locations within the field of view of the cameras. The 3D position of the tool and the 3D position of the structured light endoscope, for example, may be 3D positions of the markers on the tool and 3D positions of the markers on the structured light endoscope, respectively. The processor may also determine an orientation of the tool and/or an orientation of the structured light endoscope based on relative orientations of the markers of the tool and the markers of the structured light endoscope, respectively. In one embodiment, the tool and/or the structured light endoscope do not include markers, and the processor determines the 3D position of the tool and/or the 3D position of the structured light endoscope based on surface features of the tool and/or the structured light endoscope, respectively. In other embodiments, other methods and systems may be used to determine the 3D position of the tool and/or the 3D position of the structured light endoscope. For example, the 3D position of the tool and the 3D position of the structured light endoscope may be estimated directly from images or structured light images using tool detection.

The processor may identify the tool and/or the structured light endoscope being used in, for example, the laparoscopic surgery. In one embodiment, a user identifies a type of the tool and/or a type of the structured light endoscope via, for example, one or more inputs (e.g., a keyboard and a mouse). In another example, the processor automatically identifies the tool and/or the structured light endoscope being used in the laparoscopic surgery, for example, based on data (e.g., identifying data) received from the tool and/or data (e.g., identifying data) received from structured light endoscope, respectively, or the image data generated by the cameras.

For example, the processor may match image data, which is generated by the cameras and includes a representation of the tool and/or a representation of the structure light endoscope, with stored data corresponding to different types of tools and/or endoscopes. The processor may match characteristics of the tool and/or characteristics of the structured light endoscope within the generated image data to characteristics of tools and/or characteristics of endoscopes within the stored data, respectively, to identify the type of the tool and/or the type of the endoscope being used. For example, a particular endoscope (e.g., the structured light endoscope) may include a unique combination of number of markers and size and markers. The processor may identify a number of markers and a size of the markers on an endoscope (e.g., characteristics) within image data generated by the cameras, and may identify that the particular structured light endoscope is being used based on a comparison of the identified characteristics with descriptions of a plurality of different types of endoscopes (e.g., different manufacturers, different models). For example, the memory may store data describing the plurality of different types of endoscope, and the stored data describing the particular structured light endoscope may specify that the particular structured light endoscope includes four markers of a particular size.

Based on the identified type of the tool and the identified position and orientation of the tool, the processor may determine a 3D position of a proximal end of the tool in the 3D space. For example, with the known type of the tool, a length of the tool may be identified (e.g., from the stored data corresponding to different types of tools), and the processor may determine the 3D position of the proximal end of the tool in the 3D space based on the identified length of the tool and the identified 3D positions of the markers on the tool. Further, based on the identified type of the endoscope and the identified position and orientation of the endoscope, the processor may determine a 3D position of a proximal end of the endoscope (e.g., the structured light endoscope) within the 3D space.

The processor identifies a representation (e.g., a 3D model) of the tool based on the identified type of the tool. In one embodiment, the memory stores a plurality of 3D models for respective tools, and the processor identifies the 3D model of the tool from the plurality of stored 3D models based on the identified type of the tool. For example, the processor identifies the tool being used within the laparoscopic surgery is a particular trocar based on characteristics identified within the image data generated by the cameras. The processor selects a 3D model for the particular trocar from the plurality of stored 3D models for respective tools based on the identification of the tool. In other embodiments, the processor generates the 3D model of the tool in real time based on the determined 3D position of the tool, the determined orientation of the tool, the identified type of the tool, stored data related to the identified tool (e.g., characteristics of the tool such as size and shape of the tool), other information related to the identified tool, or any combination thereof.

In another embodiment, the processor determines a shape and a size of the tool based on the image data generated by the cameras, an endoscope, or another imaging device (e.g., from act 102). The processor generates the 3D model of the tool based on the determined shape and the determined size of the tool.

The processor may also determine a position of the tool relative to the endoscope (e.g., the structured light endoscope). The processor may determine the position of the tool relative to the structured light endoscope based on the 3D position of the tool and the 3D position of the structured light endoscope determined within the same 3D space. For example, the 3D position of the structured light endoscope may be subtracted from the 3D position of the tool. Based on the determined position of the tool relative to the structured light endoscope and the viewpoint from which the 3D model is generated in act 104, the processor may also determine the 3D position of the tool relative to the 3D model of the surface of the object.

The processor generates the first augmented 3D model by fusing the 3D model of the tool with the 3D model of the surface of the object based on the determined 3D position of the tool relative to the 3D model of the surface of the object. In one embodiment, the 3D model of the tool and the 3D model of the surface of the object are already registered. In another embodiment, the 3D model of the tool and the 3D model of the surface of the object are registered in any number of ways including, for example, with 3D/3D registration.

Figure 3:
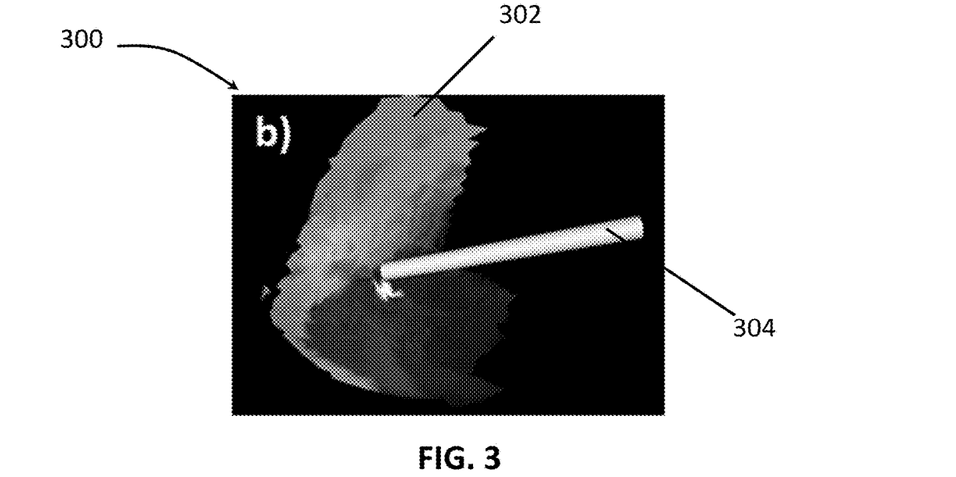
FIG. 3 shows an example of a first augmented three-dimensional (3D) model.
Figure 4:
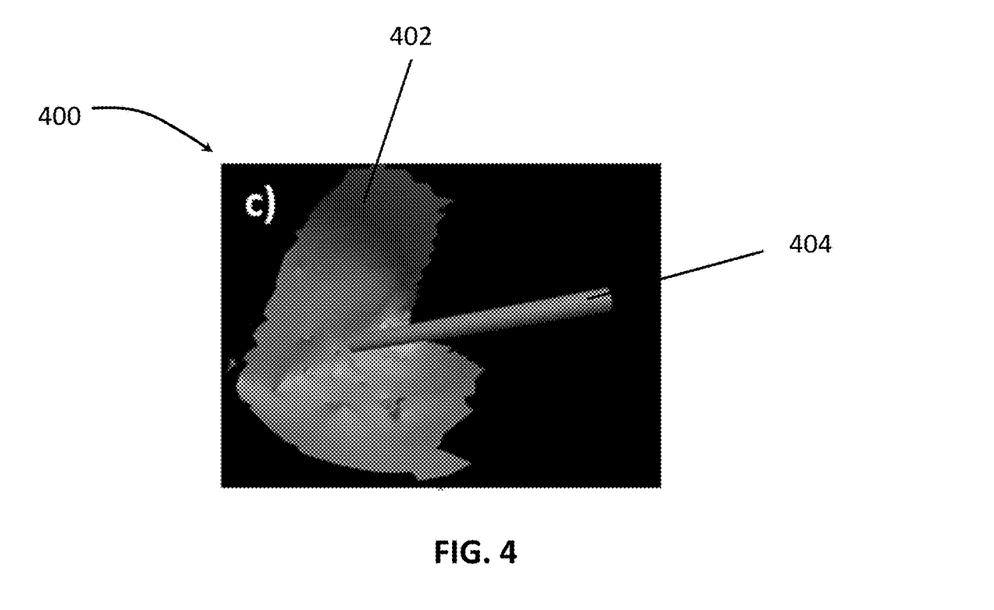
FIG. 4 shows another example of a first augmented 3D model.

FIG. 3 shows an example of a first augmented 3D model 300. The first augmented 3D model 300 includes a 3D model 302 of the surface of the object identified in act 104 and a 3D model 304 of the tool generated in act 106. The 3D model 302 of the surface of the object shown in FIG. 3 includes a textured representation of the surface of the object. FIG. 4 shows another example of a first augmented 3D model 400. The first augmented 3D model 400 includes a 3D model 402 of the surface of the object identified in act 104 and a 3D model 404 of the tool generated in act 106. The 3D model 402 of the surface of the object shown in FIG. 4 includes an untextured representation of the surface of the object.

In act 108, the processor introduces a virtual light source into the first augmented 3D model generated in act 106. The virtual light source may be introduced into the first augmented 3D model in an up vector from the image identified in act 102. In one embodiment, the virtual light source is introduced into the first augmented 3D model at a position upwards of gravity, as defined by the optical tracking system. In another embodiment, the virtual light source is introduced into the first augmented 3D model, such that the virtual light source is co-located with a real light source. The virtual light source thus creates shadows in a similar configuration to real shadows that are faint or not visible in the image identified in act 102, for example. This has the effect of enhancing the existing faint shadow.

In act 110, the processor generates a second augmented 3D model. The processor generates a representation of a shadow on the surface of the object in the generated first augmented 3D model based on the virtual light source introduced into the generated first augmented 3D model. The second augmented 3D model includes the fused 3D model of the tool and the 3D model of the surface of the object and the generated representation of the shadow.

Figure 5:
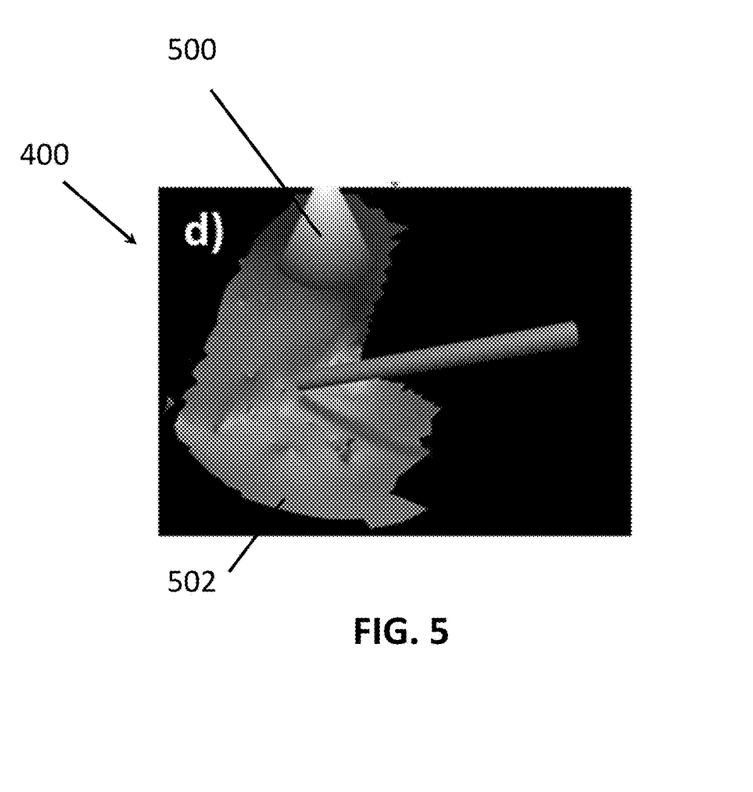
FIG. 5 shows an example of a virtual light source introduced into the example of the first augmented 3D model shown in FIG. 4.

FIG. 5 shows an example of a virtual light source 500 introduced into the example of the first augmented 3D model 400 shown in FIG. 4. The processor generates the representation of the shadow 502 based on the virtual light source 500 introduced into the first augmented 3D model in act 108. The processor estimates the shadow 502 that is cast on the surface of the object within the first augmented 3D model 400 by the 3D model 404 of the tool.

Figure 6:
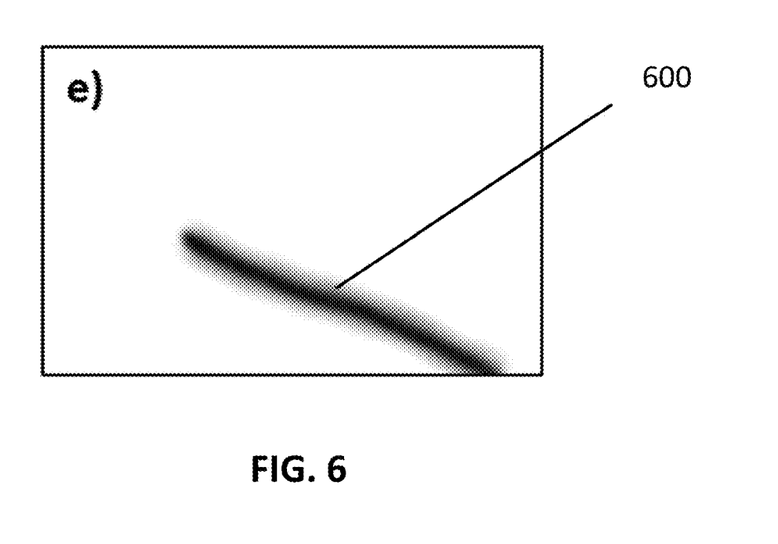
FIG. 6 shows an example of a representation of a virtual shadow after the first augmented 3D model has been subtracted from the second augmented 3D model.

In act 112, the processor augments the identified image of the surface of the object. The processor subtracts the first augmented 3D model generated in act 106 from the second augmented 3D model generated in act 110. After the subtraction, a representation of a virtual shadow remains. FIG. 6 shows an example of a representation of a virtual shadow 600 after the first augmented 3D model has been subtracted from the second augmented 3D model.

In one embodiment, a darkness and a transparency of the representation of the virtual shadow 600 is controllable via a user interface (e.g., a GUI) to identify a working region of the tool. As the tool gets closer to the surface of the object, the shadow formed by the tool gets darker. A darker shadow may occlude information on the surface of the object. Accordingly, the processor may lighten the representation of the shadow, or the representation of the shadow may be visualized with a border of the shadow.

The augmenting of the identified image of the surface of the object includes superimposing the generated representation of the shadow on the image of the surface of the object and the tool identified in act 102. For example, the generated representation of the shadow may be fused with the image identified in act 102. In one embodiment, the representation of the virtual shadow is rendered separately and blended.

In one embodiment, the image of the surface of the object and the tool identified in act 102 and the representation of the virtual shadow are already registered since the 3D model of the surface of the object identified in act 104 and the image identified in act 102 are from the same viewpoint. In another embodiment, the image of the surface of the object and the tool identified in act 102 and the representation of the virtual shadow are registered in any number of ways including, for example, with 2D/2D registration.

Figure 7:
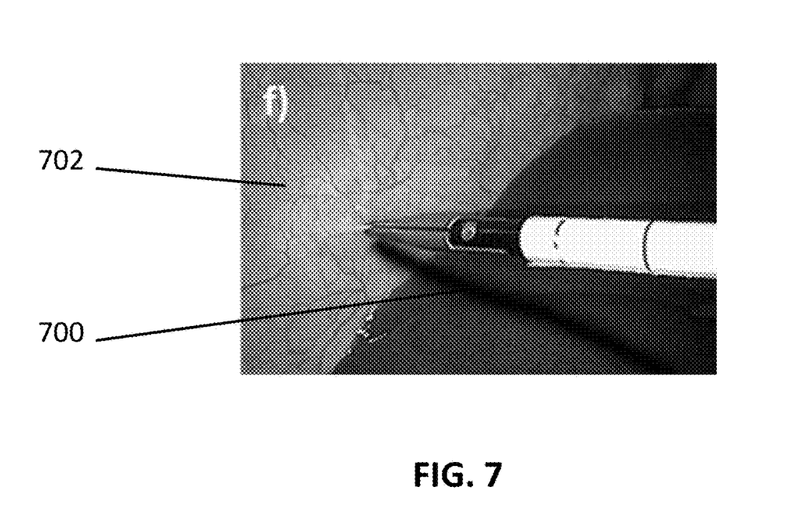
FIG. 7 shows an example of a generated representation of a virtual shadow fused with an image of a surface of an object and a tool.

FIG. 7 shows an example of a generated representation of a virtual shadow 700 fused with an image 702 of a surface of an object and a tool (e.g., the image identified in act 102). The introduction of the virtual shadow 700 into the image 702 of the surface of the object and the tool provides augmented reality. With the use of, for example, a structured light laparoscope, a 3D model of the surface of the object and thus the representation of the shadow may be generated in real time. The introduction of the representation of the shadow into laparoscopic images and/or video in real time enables surgical procedures to be performed faster and more efficiently with fewer errors. Also, the introduction of the representation of the shadow may make learning laparoscopic surgical techniques and skills easier.

Figure 8:
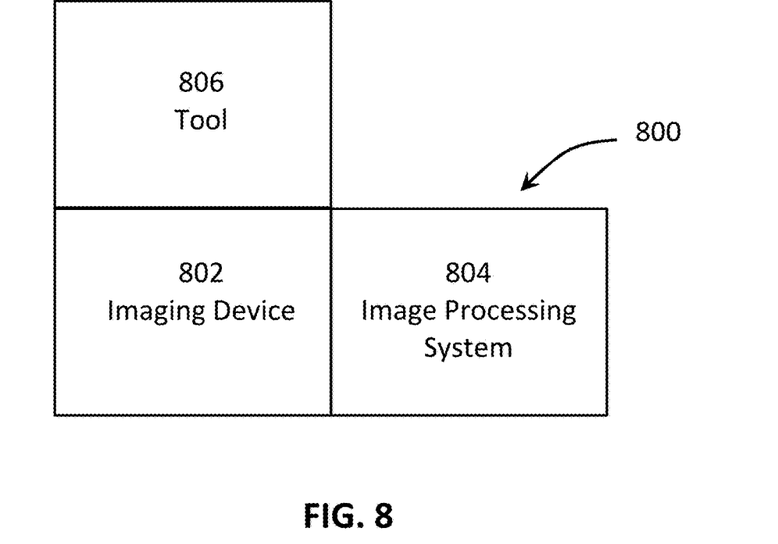
FIG. 8 shows one embodiment of an image-guided system.

FIG. 8 shows one embodiment of an image-guided system 800. The image-guided system 800 may be used in the method described above and the system described below. The image-guided system 800 may include one or more imaging systems 802 (e.g., an endoscopy system), one or more image processing systems 804 (e.g., an image processing system), and one or more tools 806 (e.g., a tool). A dataset representing a two-dimensional (2D) or a three-dimensional (3D) (e.g., volumetric) region may be acquired using the imaging device 802 and the image processing system 804 (e.g., an imaging system). The 2D dataset or the 3D dataset may be obtained contemporaneously with the panning and/or execution of a medical treatment procedure or at an earlier time. Additional, different or fewer components may be provided.

In one embodiment, the imaging system 802, 804 is, for example, an endoscope. The imaging system 802, 804 may be used to create a patient model that may be used during a medical procedure (e.g., a laparoscopic surgery). For example, the image processing system 804 is a workstation for laparoscopic surgery within the abdomen of a patient. In other embodiments, the imaging system 102, 104 may include, for example, a medical workstation, a magnetic resonance imaging (MRI) system, a computed tomography (CT) system, an ultrasound system, a positron emission tomography (PET) system, an angiography system, a fluoroscopy, an x-ray system, any other now known or later developed imaging system, or any combination thereof. The workstation 804 receives data representing or images of the patient (e.g., including at least part of the abdomen of the patient) generated by the imaging device 802.

The tool 806 may be image guided by the imaging system 802, 804. The tool 806 may be any number of tools including, for example, a trocar, forceps, scissors, a probe, a dissector, hooks, retractors, or other medical devices. The tool 806 may be used, for example, to image, close wounds, take biopsies, cut, drain fluids, or grasp tissue. The tool 806 may be image guided to facilitate diagnosis or treatment. The position, transmission, or other operation of the tool 806 may be controlled by the image processing system 804 or another controller. The image-guided system 800 may include more or fewer components.

Figure 9:
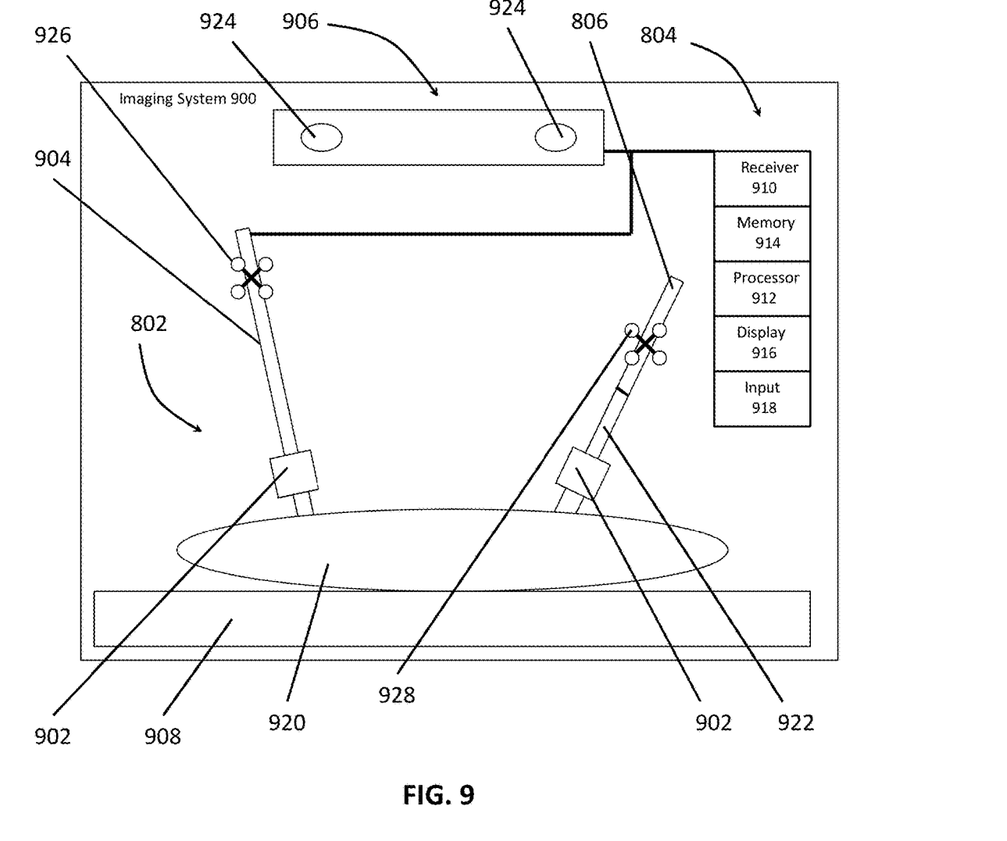
FIG. 9 shows one embodiment of an imaging system.

FIG. 9 shows one embodiment of an imaging system 900. The imaging system 900 includes the endoscopy system 802 and the image processing system 804. The endoscopy system 802 includes one or more ports 902 (e.g., two ports), an endoscope 904, an optical tracking system 906, and a patient bed 908. The image processing system 804 may include a receiver 910, a processor 912, a memory 914, and a display 916. Additional, different, or fewer components may be provided. For example, an additional endoscope may be provided for imaging. Additionally, a user input device 918 (e.g., a keyboard and/or a mouse) may be provided for user control.

In one embodiment, the processor 912 and the memory 914 are part of the endoscopy system 802. Alternatively, the processor 912 and the memory 914 are part of an archival and/or image processing system, such as associated with a medical records database workstation or server. In yet other embodiments, the processor 912 and the memory 914 are a personal computer such as a desktop or a laptop, a workstation, a server, a network, or combinations thereof. The processor 912 and the memory 914 may be provided without other components for implementing the method.

The patient bed 908 (e.g., a patient gurney or table) supports an examination subject 920 such as, for example, a patient. In order to examine and/or operate on the patient, the endoscope 904 is inserted into one of the ports 902, and the endoscope 904 generates image data for a portion of the patient within a field of view. The endoscope 904 may include any number of parts including, for example, a tube (e.g., a rigid or flexible tube), a light delivery system to illuminate the portion of the patient, a lens system, an eyepiece, a camera, or any combination thereof. In one embodiment, the endoscope 904 is a structured light endoscope that illuminates the portion of the patient via fiberoptics, and generates image data with a camera. The endoscope 904 generates and transmits image data to the receiver 910.

The tool 806 is inserted into another one of the ports 902. In one embodiment, a hollow cannula 922 is inserted into the other port 902, and the tool 806 is inserted into the hollow cannula 922. The tool 806 is guided within the patient based on images generated by the endoscope 904 or another endoscope.

The endoscope 904 connects with the receiver 910. The connection is wired (e.g., using a coaxial cable) or wireless. The connection is for image data from the endoscope 904 to be transmitted to and received by the receiver 910. The receiver 910 includes the processor 912 or another processor (e.g., a digital signal processor, a field programmable gate array, or an application specific circuit for applying an inverse Fourier transform) for generating an image based on the image data generated by the endoscope 904. The receiver 910 is configured by hardware or software.

The processor 912 is a general processor, a central processing unit, a control processor, a graphics processor, a digital signal processor, a three-dimensional rendering processor, an image processor, an application-specific integrated circuit, a field-programmable gate array, a digital circuit, an analog circuit, combinations thereof, or other now known or later developed device for image processing. The processor 912 is a single device or multiple devices operating in serial, parallel, or separately. The processor 912 may be a main processor of a computer, such as a laptop or desktop computer, or may be a processor for handling some tasks in a larger system, such as being part of the receiver 910 or the imaging system 804. The processor 912 is configured by instructions, design, hardware, and/or software to perform the acts discussed herein, such as augmenting an image of a surface.

The memory 914 is a computer readable storage media. The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 914 may be a single device or a combination of devices. The memory 914 may be adjacent to, part of, networked with and/or remote from the processor 912.

The display 916 is a monitor, a CRT, an LCD, a plasma screen, a flat panel, a projector or other now known or later developed display device. The display 916 is operable to generate images for a two-dimensional view or a rendered three-dimensional representation. For example, a two-dimensional image representing a three-dimensional volume through rendering is displayed.

The optical tracking system 906 includes one or more (e.g., two) cameras 924, first markers 926 (e.g., optical markers), and/or second markers 928 (e.g., optical markers). The two cameras 924, for example, are positioned, such that the first markers 926 and the second markers 928 are within the field of view of the two cameras 924. The cameras 924 may be fixed or positionable such that the first markers 926 and the second markers 928 are within the field of view of the two cameras 924.

The first markers 926 are positioned on the endoscope 904, and the second markers 928 are positioned on the tool 806. The first markers 926 and the second markers 928 may be any number of sizes and/or shapes. For example, the first markers 926 and the second markers 928 may be spherical in shape and may be sized such that the first markers 926 and the second markers 928 are visible within images generated by the cameras 924. Other shapes and/or sizes may be provided. In the embodiment shown in FIG. 9, the first markers 926 include four first markers 926, and the second markers 928 include four second markers 928. More or fewer first markers 926 and/or second markers 928 may be provided. The first markers 926 and the second markers 928 may be positioned in any number of patterns relative to each other (e.g., x-shaped pattern) and/or may be positioned in any number of locations along the endoscope 904 and the tool 806, respectively.

In one embodiment, the memory 914 is configured to store an image of a surface (e.g., an internal surface) of, for example, the patient 920 and at least a portion of the tool 806. The memory is also configured to store a 3D model of the surface of the patient 920. The processor 912 is configured to superimpose a representation of the tool 806 on the identified 3D model of the surface of the patient 920. The processor 912 is also configured to introduce a virtual light source into the superimposed representation of the tool 806 and identified 3D model of the surface of the patient 920, for example. The processor 912 is configured to generate a representation of a shadow on the surface of the patient 920 within the superimposed representation of the tool 806 and identified 3D model of the patient 920 based on the introduced light source. The processor 912 is configured to superimpose the generated representation of the shadow on the stored image of the surface of the patient 920 and at least the portion of the tool 806.

In one embodiment, one or more endoscopes (e.g., the endoscope 904) are configured to generate first data representing the surface of the object, and generate second data representing the surface of the object. The processor 912 is further configured to generate the 3D model of the surface of the patient 920 based on the generated first data, and generate the image of the surface of the patient 920 and at least the portion of the tool 806 based on the generated second data.

In one embodiment, the optical tracking system 906 is configured to determine a 3D position of the tool 806 relative to the 3D model of the surface of the patient 920. The one or more cameras 924 are positioned at a distance away from the patient 920. The one or more cameras 924 are configured to generate image data for the first markers 926 positioned on the endoscope 904 and the second markers 928 positioned on the tool 806. The processor 912 is further configured to identify a 3D model of the tool 806 from a plurality of predetermined models of tools stored in the memory 914 based on the tool 806 (e.g., a type of tool) being used. Alternatively, the processor 912 is configured to determine a shape and a size of the tool 806 based on the image of the surface of the patient 920 and at least the portion of the tool 806 stored in the memory 914. The processor 912 is further configured to generate the 3D model of the tool 806 based on the determined shape and the determined size of the tool 806.

The processor 912 is configured to identify the 3D position of the tool 806 relative to the 3D model of the surface of the patient 920. The identification of the 3D position of the tool 806 relative to the 3D model of the surface of the patient 920 includes estimation of the 3D position of the tool 806 relative to the 3D model of the surface of the patient 920 based on image data for the first markers 926 positioned on the endoscope 904 and the second markers 928 positioned on the tool 806, and the identified model of the tool 806. The processor 912 is further configured to superimpose the representation of the tool 806 on the identified 3D model of the surface of the patient 920 based on the identified 3D position of the tool relative to the 3D model of the surface of the object.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for augmenting an image of a surface of an object, the method comprising:
   identifying, by a processor, the image of the surface of the object, the image of the surface of the object being an image of the surface of the object and at least a portion of a tool;
   identifying, by the processor, a three-dimensional (3D) model of the surface of the object;
   generating, by the processor, a first augmented 3D model, the generating of the first augmented 3D model comprising superimposing a representation of the tool on the identified 3D model of the surface of the object;
   introducing, by the processor, a virtual light source into the generated first augmented 3D model;
   generating, by the processor, a second augmented 3D model, the generating of the second augmented 3D model comprising generating a representation of a shadow on the surface of the object in the generated first augmented 3D model based on the virtual light source introduced into the generated first augmented 3D model; and
   augmenting, by the processor, the identified image of the surface of the object, the augmenting of the identified image of the surface of the object comprising superimposing the generated representation of the shadow on the identified image of the surface of the object.

2. The method of claim 1, wherein identifying the image of the surface of the object comprises:
   generating, by a laparoscope, image data representing the surface of the object; and
   generating, by the processor, the image of the surface of the object based on the generated image data.

3. The method of claim 1, wherein identifying the 3D model of the surface of the object comprises:
   generating, by an endoscope, data representing the surface of the object; and generating, by the processor, the 3D model of the surface of the object based on the generated data.

4. The method of claim 3, wherein the identified image of the surface of the object is from a viewpoint, and
wherein generating the 3D model of the surface of the object comprises generating the 3D model of the surface of the object based on the generated data from the viewpoint.

5. The method of claim 3, wherein the endoscope is a structured light endoscope,
wherein generating the data representing the surface of the object comprises:
generating, with the structured light endoscope, a point cloud of the surface of the object; and
generating, with the processor, a mesh of the surface of the object based on the generated point cloud, and
wherein generating the 3D model of the surface of the object based on the generated data comprises generating the 3D model of the surface of the object based on the generated mesh of the surface of the object.

6. The method of claim 5, further comprising identifying a position of the tool.

7. The method of claim 6, wherein identifying the position of the tool comprises identifying, by an optical tracking system, a 3D position of the tool relative to the 3D model of the surface of the object.

8. The method of claim 7, wherein the optical tracking system comprises:
one or more markers positioned on the tool;
one or more markers positioned on the structured light endoscope; and
one or more cameras positioned at a distance away from the object, the one or more cameras being configured to generate image data for the one or more markers of the tool and the one or more markers of the structured light endoscope,
wherein the method further comprises identifying, by the processor, a 3D model of the tool, and
wherein identifying the 3D position of the tool relative to the 3D model of the surface of the object comprises estimating the 3D position of the tool relative to the 3D model of the surface of the object based on the image data for the one or more markers of the tool and the one or more markers of the structured light endoscope, and the identified 3D model of the tool.

9. The method of claim 7, wherein identifying the 3D model of the tool comprises:
identifying, by the processor, the 3D model of the tool from a plurality of predetermined models of tools stored in a memory based on the tool being used, the memory being in communication with the processor; or
determining, by the processor, a shape and a size of the tool based on the identified image of the surface of the object and at least the portion of the tool, and generating, by the processor, the 3D model of the tool based on the determined shape and the determined size of the tool.

10. The method of claim 1, wherein introducing the virtual light source into the generated first augmented 3D model comprises introducing the virtual light source into the generated first augmented 3D model in an up vector from the identified image, or at a position upwards of gravity, as defined by an optical tracking system configured to identify a position of the tool.

11. The method of claim 1, further comprising subtracting, by the processor, the generated first augmented 3D model from the generated second augmented 3D model, such that the representation of the shadow remains.

12. The method of claim 11, wherein augmenting the identified image of the surface of the object comprises blending or fusing the representation of the shadow with the identified image of the surface of the object.

13. In a non-transitory computer-readable storage medium storing instructions executable by one or more processors to augment an image of a surface of an object, the instructions comprising:
identifying, by a processor, the image of the surface of the object, the image of the surface of the object being an image of the surface of the object and at least a portion of a tool;
identifying, by the processor, a three-dimensional (3D) model of the surface of the object;
superimposing, by the processor, a representation of the tool on the identified 3D model of the surface of the object;
introducing, by the processor, a virtual light source into the superimposed representation of the tool and identified 3D model of the surface of the object;
generating, by the processor, a representation of a shadow on the surface of the object within the superimposed representation of the tool and identified 3D model of the surface of the object based on the introduced light source; and
superimposing, by the processor, the generated representation of the shadow on the identified image of the surface of the object.

14. The non-transitory computer-readable storage medium of claim 13, wherein the surface of the object is an internal surface of a body of a patient.

15. The non-transitory computer-readable storage medium of claim 13, wherein the instructions further comprise identifying a position of the tool, the identifying of the position of the tool comprising identifying, by an optical tracking system, a 3D position of the tool relative to the 3D model of the surface of the object.

16. The non-transitory computer-readable storage medium of claim 15, wherein the optical tracking system comprises:
one or more markers positioned on the tool;
one or more markers positioned on the structured light endoscope; and
one or more cameras positioned at a distance away from the object, the one or more cameras being configured to generate image data for the one or more markers of the tool and the one or more markers of the structured light endoscope,
wherein the instructions further comprise identifying, by the processor, a 3D model of the tool, and
wherein identifying the 3D position of the tool relative to the 3D model of the surface of the object comprises estimating the 3D position of the tool relative to the 3D model of the surface of the object based on the image data for the one or more markers of the tool and the one or more markers of the structured light endoscope, and the identified 3D model of the tool.

17. The non-transitory computer-readable storage medium of claim 15, wherein identifying the 3D model of the tool comprises:
identifying, by the processor, the 3D model of the tool from a plurality of predetermined models of tools stored in a memory based on the tool being used, the memory being in communication with the processor; or determining, by the processor, a shape and a size of the tool based on the identified image of the surface of the object and at least the portion of the tool, and generating, by the processor, the 3D model of the tool based on the determined shape and the determined size of the tool.

18. A system for generating an augmented image of a surface of an object and at least a portion of a tool, the system comprising:
a memory configured to store:
an image of the surface of the object and at least the portion of the tool; and
a three-dimensional (3D) model of the surface of the object; and
a processor in communication with the memory, the processor being configured to:
superimpose a representation of the tool on the identified 3D model of the surface of the object;
introduce a virtual light source into the superimposed representation of the tool and identified 3D model of the surface of the object;
generate a representation of a shadow on the surface of the object within the superimposed representation of the tool and identified 3D model of the surface of the object based on the introduced light source; and
superimpose the generated representation of the shadow on the stored image of the surface of the object and at least the portion of the tool.

19. The system of claim 18, further comprising:
one or more endoscopes configured to:
generate first data representing the surface of the object; and
generate second data representing the surface of the object,
wherein the processor is further configured to:
generate the 3D model of the surface of the object based on the generated first data; and
generate the image of the surface of the object and at least the portion of the tool based on the generated second data.

20. The system of claim 19, further comprising an optical tracking system configured to determine a 3D position of the tool relative to the 3D model of the surface of the object, the optical tracking system comprising:
one or more markers positioned on the tool;
one or more markers positioned on the endoscope; and
one or more cameras positioned at a distance away from the object, the one or more cameras being configured to generate image data for the one or more markers of the tool and the one or more markers of the endoscope,
wherein the processor is further configured to:
identify a 3D model of the tool, the identification of the 3D model of the tool comprising:
identification of the 3D model of the tool from a plurality of predetermined models of tools stored in the memory based on the tool being used; or
determination of a shape and a size of the tool based on the stored image of the surface of the object and at least the portion of the tool, and generation of the 3D model of the tool based on the determined shape and the determined size of the tool; and
identify the 3D position of the tool relative to the 3D model of the surface of the object, the identification of the 3D position of the tool relative to the 3D model of the surface of the object comprising estimation of the 3D position of the tool relative to the 3D model of the surface of the object based on the image data for the one or more markers of the tool and the one or more markers of the structured light endoscope, and the identified 3D model of the tool, and
wherein the processor is configured to superimpose the representation of the tool on the identified 3D model of the surface of the object based on the identified 3D position of the tool relative to the 3D model of the surface of the object.

* * * * *